United States Patent [19]

Nagaoka et al.

[11] 4,424,311
[45] Jan. 3, 1984

[54] ANTITHROMBOGENIC BIOMEDICAL MATERIAL

[75] Inventors: Shoji Nagaoka; Hidefumi Takiuchi; Yuichi Mori, all of Kamakura; Tetsuya Kikuchi, Yokohama, all of Japan

[73] Assignee: Toray Industries, Incorporated, Tokyo, Japan

[21] Appl. No.: 393,655

[22] Filed: Jun. 30, 1982

[30] Foreign Application Priority Data

Jul. 1, 1981 [JP] Japan .................................. 56/101331

[51] Int. Cl.$^3$ ........................................ C08F 259/04
[52] U.S. Cl. ........................... 525/303; 525/312; 526/313; 526/320; 526/333
[58] Field of Search ................. 526/320, 313, 333; 523/112; 525/312, 303

[56] References Cited

U.S. PATENT DOCUMENTS

| | | | |
|---|---|---|---|
| 3,392,137 | 7/1968 | Slocombe | 526/320 |
| 4,028,295 | 6/1977 | Loshaek | 526/320 |
| 4,038,264 | 7/1977 | Rostoker | 526/320 |
| 4,170,582 | 10/1979 | Mori | 526/320 |
| 4,200,563 | 4/1980 | Komiya | 526/320 |
| 4,279,795 | 7/1981 | Yamashita | 523/112 |
| 4,306,780 | 12/1981 | Tarumi | 526/313 |

OTHER PUBLICATIONS

Photo Induced Block and Graft Polymerization of Methoxy Polyethylene Glycol Monomethacrylate to Vinyl Polymers, H. Miyama, et al., J. Polymer Sci., 10:2469-71 (1972).

Dependence of Albumin–Fibrinogen Simple and Competitive Adsorption on Surface Properties of Biomaterial, J. L. Brash and S. Uniyal, J. Polymer Sci., Polymer Symposium 66:377-389 (1979).

New Synethetic Membranes for Dialysis, I. A. Copolymer–Ester Membrane, System, D. J. Lyman, et al., Biochemistry, 3(7):985-990 (1964).

Effects of a Polyoxyethylene Detergent (BRIJ 58) On Platelet Aggregation, Release and Clotting Activity, P. G. Barton, Biochimica et Biophys. Acta., 539:98-113 (1978).

Preparation of a Non–Immunogenic Arginase by the Covalent Attachment of Polyethylene Glycol, K. V. Savoca, et al., Biochmica et Biophys. Acta., 578:47-53 (1979).

Primary Examiner—Paul R. Michl
Attorney, Agent, or Firm—Scully, Scott, Murphy & Presser

[57] ABSTRACT

Provided is an antithrombogenic biomedical material comprising a copolymer of (A) not less than 5% by weight of one or more polymerizable monomers having a polyethylene oxide unit with a degree of polymerization not less than 5 and a polymerizable carbon-carbon double bond and (B) not more than 95% by weight of one or more monomers copolymerizable with said monomer (A).

9 Claims, No Drawings

ANTITHROMBOGENIC BIOMEDICAL MATERIAL

BACKGROUND OF THE INVENTION

The present invention relates to an antithrombogenic biomedical material.

In recent years, along with increased utilzation of polymeric materials in the medical field, increasing attention has been paid to hydrophilic polymers and particularly water-insoluble and water-absorbing polymers have come to be used as materials of various membranes, catheters, cannulae, medical supplies, contact lenses, blood preservation vessels, blood circuits and cell culturing substrates, and also as embedding (entrapping) substrates for enzymes and medicines. Furthermore, such materials are applicable not only to the medical field but also to carriers for electrophoresis and liquid chromatography, various coating materials for the prevention of stain, dulling, etc. and food-related materials.

For such a purpose, there have heretofore been used hydrogels comprising synthetic polymers containing hydrophilic components such as 2-hydroxyethyl methacrylate (hereinafter referred to simply as "HEMA"), N-vinylpyrrolidone (hereinafter referred to simply as "NVP"), acrylamide, (meth)acrylic acid and vinyl alcohol.

In general, however, hydrogels obtained from such hydrophilic monomers with a molecular weight not more than 200 tend to lose their transparency or sharply deteriorate in their mechanical strength when their permeability is tried to be enhanced. Moreover, in case these hydrogels contact with blood, body fluids or living tissue, adsorption of various liquid components such as proteins and lipids or adhesion of cellular components such as platelets, leucocytes, erythrocytes and fibroblasts, are unavoidable. Such an adsorption or adhesion of biological components is presumed to result in the formation of thrombi on the surface of the hydrogels, deterioration of the immunizing function due to activation of a complement system, or degeneration and necrosis of tissues. Deterioration of permeability and of transparency caused by the adhesion of these biological components has also been reported.

SUMMARY OF THE INVENTION

It is an object of the present invention to overcome the aforementioned disadvantages encountered in the prior arts.

It is another object of the present invention to provide a biomedical polymer having a high permeability and being effective in suppressing non-specific adhesion of biological components and superior in the biocompatibility, for example, in antithrombogenicity.

Other objects and advantages of the present invention will become apparent from the following description.

According to the present invention, there is provided an antithrombogenic biomedical material comprising a copolymer of (A) not less than 5% by weight of one or more polymerizable monomers having a polyethylene oxide unit with a degree of polymerization not less than 5 and a polymerizable carbon-carbon double bond and (B) not more than 95% by weight of one or more monomers copolymerizable with the polymerizable monomer (A).

PREFERRED EMBODIMENTS OF THE INVENTION

The copolymer of the present invention is obtained from (A) not less than 5% by weight of a polymerizable monomer having a polyethylene oxide unit with a degree of polymerization not less than 5 and a polymerizable carbon-carbon double bond and (B) not more than 95% by weight of a monomer copolymerizable with the polymerizable monomer (A).

The copolymerization may be carried out by a random copolymerization of the monomers (A) and (B), or by polymerizing the monomer (B) in advance and graft or block polymerizing the monomer (A) to the resulting polymer.

As the monomer (A) there essentially may be used any addition-polymerizable monomers having in one molecule a polymerizable carbon-carbon double bond such as vinyl group and a polyethylene oxide unit with a degree of polymerization not less than 5. Examples are (meth)acrylates represented by the following general formula (1):

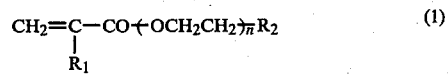
(1)

where $n \geq 5$,
$R_1$ is hydrogen or $CH_3$,
$R_2$ is hydroxyl, $C_1$-$C_4$ alkoxy or $CHPh_2$ where Ph is phenyl,
and vinyl monomers represented by the following general formula (2):

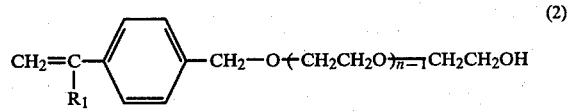
(2)

where $n \geq 5$,
$R_1$ is hydrogen or $CH_3$.

These addition-polymerizable monomers and their manufacturing methods are known. For example, polyethylene glycol mono(meth)acrylate of the formula (1) can be obtained by reaction of the corresponding polyethylene glycol and methyl (meth)acrylate. More particularly, for example, a compound of the formula (1) with $R_1$ being $CH_3$ and $R_2$ being $OCH_3$ can be obtained by interesterification reaction of a polyethylene glycol monomethyl ether resulting from the addition (addition number: $n \geq 5$) of ethylene oxide to methanol and methyl methacrylate. Moreover, by an anionic polymerization of ethylene oxide using diphenylmethyl potassium as an initiator and by terminating the reaction with methacrylic acid chloride, there can be obtained a compound wherein $R_1$ is $CH_3$ and $R_2$ is $CHPh_2$.

The degree of polymerization (n) of polyethylene oxide units in these monomers (A) can be determined by measuring the molecular weight of the compound by gel permeation chromatography or other suitable means. It is necessary that the degree of polymerization (n) be not less than 5. Particularly, its range between 9 and 300 is preferred.

These monomers (A) have a polymerizable carbon-carbon double bond and therefore, even without using a special apparatus or method, they can be polymerized easily by using conventional radical initiators such as, for example, azobisisobutyronitrile, azobisdimethyl valeronitrile and benzoyl peroxide. Also, they can be copolymerized with other monomers or polymers and can form polymer compositions having polyethylene oxide units in high efficiency and reproducibility.

It is essential that monomer (A) be present in the resulting copolymer in an amount of 5 to 95% by weight in terms of monomer. Usually its content ranges from 10 to 95% by weight, more preferably 15 to 90% by weight.

In case the degree of polymerization (n) of polyethylene oxide units is lower than 5 and the amount of monomer (A) is smaller than 5% by weight, a medical application of the resulting copolymer will allow easy adhesion of various biological components and its permeability will be inferior.

As the monomer which affords the other portion than monomer (A) in the resulting copolymer, there essentially may be used any monomer if only it is copolymerizable with monomer (A). Examples of such a monomer include addition-polymerizable compounds having a carbon-carbon double bond and mixtures thereof, such as acrylic acid, methacrylic acid, methyl acrylate, methyl methacrylate, dimethylaminoethyl methacrylate, acrylonitrile, vinyl acetate, vinyl chloride, styrene, vinylidene chloride, vinylidene fluoride, 2-hydroxyethyl methacrylate, N-vinylpyrrolidone, acrylamide, diacetone acrylamide, ethylene, propylene and butadiene.

As previously noted, the copolymerization of monomers (A) and (B) may be carried out in any desired manner. Particularly, a random copolymerization of both and a graft or block copolymerization of monomer (A) with a polymer of monomer (B) are preferred.

In case a hydrophilic compound is used as monomer (B) there may be added, if required, 0.001 to 10% by weight of a cross-linking component (C) for preventing the resulting polymer from being dissolved out into water. As such a cross-linking component there may be used monomers containing at least two polymerizable carbon-carbon double bond in the molecule, for example, ethylene glycol dimethacrylate, diethylene glycol dimethacrylate, divinylbenzene and methylenebisacrylamide.

In the graft copolymerization it is preferable to use a polymer of vinyl chloride as a trunk polymer. In this case, in addition to a vinyl chloride homopolymer, there preferably are employable copolymers of vinyl chloride with other vinyl monomers, for example, a vinyl chloride—vinyl acetate copolymer and a vinyl chloride—vinyl acetate—ethylene terpolymer. In the case of copolymers, it is preferable that they contain not less than 10% by weight of vinyl chloride units, in order to allow many features of polyvinyl chloride to be fully exhibited.

As the method of graft copolymerization, there may be used a method in which monomer (A) is heat-polymerized in the presence of a polymer of monomer (B) using a radical initiator such as benzoyl peroxide to allow chain transfer to take place to obtain a graft copolymer. But a so-called photo-initiated graft copolymerization is more preferable in which a photosensitive group is introduced in the polymer of (B) to allow photolysis to take place to produce a radical and with this radical the monomer (A) is grafted to the polymer of (B). Because, it is possible to define the quantity, structure and position of active groups and to obtain a molecular-designed, high degree of graft of a graft copolymer as compared with the foregoing graft copolymerization based on chain transfer method.

Preferred examples of such a photosensitive group are N,N-dialkyldithiocarbamate groups, and particularly diethyldithiocarbamate group (DTC group) is preferred in view of its easiness of introduction and a high stability of the resulting product. DTC group is easily introduced particularly into polymers containing vinyl chloride units. For example, a photosensitive trunk polymer is easily obtainable by mixing a polymer containing vinyl chloride units and sodium diethyldithiocarbamate in N,N-dimethylformamide and heating the mixture at 50°–60° C.

Photo-initiated graft copolymerization of monomer (A) to the trunk polymer can be effected easily by dissolving both in a solvent such as tetrahydrofuran, dimethylformamide or cyclohexanone and then radiating light having a wave length of the ultraviolet portion by means of a high pressure mercury lamp or the like. In the graft copolymerization there may be co-existent other copolymerizable monomer than the polymer of monomer(B). Examples of such a copolymerizable monomer include methacrylates such as methyl methacrylate, ethyl methacrylate and 2-hydroxyethyl methacrylate, as well as styrene and vinyl acetate.

The copolymer of the present invention has an equilibrium water content of 5 to 90% at 25° C. Equilibrium water content (W) is defined as follows:

$$W = \frac{G_2 - G_1}{G_2} \times 100 \, (\%)$$

$G_1$: Dry weight of copolymer
$G_2$: Hydrated weight of copolymer

If the equilibrium water content is lower than 5%, it is difficult to achieve the objects of the present invention, and if it exceeds 90%, mechanical properties, e.g. strength and elongation, of the copolymer will be deteriorated, so the utility value becomes poor. Particularly preferable equilibrium water content ranges from 20 to 80%.

The copolymer of the present invention is used in medical applications as a so-called hydrogel in a hydrous state. The hydration treatment may be carried out in any desired stage between the polymerization reaction and molding operation.

The copolymer of the present invention may be molded in any manner according to desired properties and shapes, for example, it alone may be molded according to cast polymerization, melt molding, solvent casting or dipping method, or it may be molded as a blend with various synthetic resins, for example, a soft polyvinyl chloride, polyurethane and polydimethylsiloxane, or it may be coated over the surface of other synthetic resin moldings.

Adhesion of various biological components to the hydrogel of the invention can be checked by means of a scanning or transmission electron microscope, amino acid analysis, electrophoresis, ellipsometry, Fourier-transform infrared absorption spectroscopy or the like, alone or in combination.

On the other hand, evaluation of this hydrogel in medical uses, for example, evaluation of its blood compatibility, can be done by various in vitro, ex vivo or in vivo tests such as Lee-White method, extracorporeal circulation method and intra-blood vessel indwelling method. As a result of evaluation by such a method, it has been found that the hydrogel of the present invention suppresses the adhesion of cellular components, namely, platelets, leucocytes, lymphocytes, tissue cells, etc., that the adsorption of body fluid components such as proteins, lipids, organic and inorganic ions is substantially extremely small, and that the hydrogel has both practical mechanical properties such as strength, elongation and flexibility and superior permeability peculiar to hydrogel.

Such a biological component non-adherent hydrogel, for the reasons previously stated, can be effectively used particularly as a biomedical material which is brought into direct contact with blood, body fluids or living tissues. For example, it exhibits superior performances as biomedical materials such as wound protecting material, soft contact lens, membranes for artificial kidney and lung, as immobilizing or slowly releasing materials for medicines, or as materials of which is required blood compatibility such as various catheters, cannulae, blood indwelling needles, blood preserving vessels and blood pumping chamber.

The following examples serve to illustrate the invention in more detail, but should not be construed as limiting the invention thereto.

EXAMPLE 1

60 g. of methoxypolyethylene glycol methacrylate "M-23G" (degree of polymerization of polyethylene oxide: 23, molecular weight: 1112, manufactured by Shin Nakamura Kogyo Co.) was dissolved in 40 g. of methyl methacrylate, then 30 mg. of 2,2'-azobis-(2,4-dimethylvaleronitrile) was added as a radical initiator. The stock solution of polymerization thus prepared was poured in a nitrogen atmosphere between two glass plates spaced from each other through a spacer formed of polyethylene terephthalate with a thickness of 100μ, then the glass plates were fixed with clamp and polymerization was allowed to take place at 50° C. for 16 hours, then further at 60° C., 80° C. and 100° C. for 1 hour each. Thereafter, the resultant polymer film was torn off from the glass plates and extracted with methanol and water at 60° C. for 3 days each to obtain a hydrogel free from residual monomer and impurities.

The thickness of the hydrogel measured with a spring type film thickness meter was 125μ, and the water content and visible ray transmittance of the hydrogel proved to be 62.8% and 98%, respectively.

By means of elementary analysis, moreover, the content of polyethylene oxide units in the polymer composition constituting this hydrogel proved to be 53.5% by weight.

A circular test piece 43 mm in diameter was cut out from this filmy hydrogel and set to an agitation type cell ("Standard Cell Type 52" manufactured by Amicon Co.) to check its water permeability.

Separately, a circular test piece 16 mm in diameter was cut out from the same hydrogel and checked for oxygen permeability using an apparatus for measuring oxygen permeability "K-316" (manufactured by Rika Seiki Kogyo Co.).

As a sample for comparison, there was prepared a copolymer of N-vinylpyrrolidone and methyl methacrylate in the same way, and this copolymer was subjected to the same measurements as above. Values thereby obtained are as shown in Table 1 below, from which it is seen that the hydrogel of the present invention has a superior permeability.

TABLE 1

| | Permeabilities of the hydrogel having polyethylene oxide units | | |
|---|---|---|---|
| Name of Sample | Water content (%) | Water permeability coefficient $(g^{-1} \cdot cm^3 \cdot sec)$ | Oxygen permeability coefficient $(ml(STP) \cdot cm/ cm^2 \cdot sec \cdot mmHg)$ |
| MMA/M-23G*[1] | 62.8 | $5.5 \times 10^{-13}$ | 6.2 |
| MMA/NVP*[2] | 64.0 | $3.2 \times 10^{-13}$ | 3.5 |

*[1]methyl methacrylate/M-23G copolymer
*[2]methyl methacrylate/N—vinylpyrrolidone copolymer (comparative example)

EXAMPLE 2

The hydrogel (16 mm in diameter) prepared in Example 1 was dipped in platelet rich plasma (PRP) of rabbit at 37° C. for 3 hours and thereafter the quantity of platelets adhered to the gel surface was measured with a scanning electron microscope. As a comparative sample there was prepared in the same way a copolymer of methoxypolyethylene glycol methacrylate having polyethylene oxide units with a degree of polymerization of 4 ("M-4G" manufactured by Shin Nakamura Kagaku Co.) and methyl methacrylate. The polyethylene oxide unit content and water content of the polymer composition constituting this gel proved to be 56.8% by weight and 60.2%.

The PRP used herein had been obtained by collecting blood from the carotid of rabbit using an injector, immediately transferring it into a silicone-treated test tube containing 1/10 volume of 3.8% sodium citrate solution and then centrifuging it at 200×g for 10 minutes. The number of platelets in PRP proved to be approximately 200,000 cells/μl.

The results are as set out in Table 2, from which it is seen that the quantity of platelets adhered to the surface of the hydrogel of the present invention is extremely small.

TABLE 2

| | Adhesion of platelets to the hydrogels having polyethylene oxide units | |
|---|---|---|
| Name of Sample | Number of platelets adhered (cells/mm$^2$) | Remarks |
| MMA/M-23G*[1] | $0.1 \times 10^5$ | FIG. 1 |
| MMA/M-4G*[2] | $1.6 \times 10^5$ | FIG. 2 |

*[1]methyl methacrylate/M-23G copolymer
*[2]methyl methacrylate/M-4G copolymer (comparative example)

EXAMPLE 3

20 g. of polyvinyl chloride of a polymerization degree of 1,100 containing diethyldithiocarbamate groups as photosensitive groups and 50 g. of methoxypolyethylene glycol methacrylate ("M-9G" manufactured by Shin Nakamura Kagaku Co.) having polyethylene oxide units were dissolved in 400 g. of tetrahydrofuran and then irradiated at 30° C. for 8 hours with a 100 W high-pressure mercury lamp ("UM-102" manufactured by Ushio Denki Co.) in a light source immersion type photoreactor ("ULO-6DQ" manufactured by Ushio Denki Co.) to obtain a graft copolymer (PS-1) with "M-9G" grafted to polyvinyl chloride.

The degree of graft and polyethylene oxide content of this graft copolymer proved to be 53.9% and 38.9% by weight, respectively. The degree of graft of the graft copolymers is defined as follows.

Degree of graft=(Grafted monomer (wt)/Trunk polymer (wt))×100 (%)

On the other hand, there was prepared a graft copolymer (PS-2) in the same manner as above except that the irradiation was made for 1 hour, which proved to contain 7.3% by weight of polyethylene oxide units.

The copolymers thus obtained were each dissolved in N,N-dimethylformamide to a concentration of 5%, and catheter-like tubes were formed from PS-1 and PS-2 according to the dipping method using as a core a stainless steel rod 1.5 mm in diameter and about 30 cm in length.

The dipping was repeated ten times and the drying was performed in a nitrogen gas stream at 63° C. The drying time between dipping operations was about 10 minutes. After dipping, the tubes were allowed to swell in methanol, then drawn out from the stainless steel rods and extracted in 60° C. methanol and water for 3 days each. Then, after vacuum drying for 48 hours, the tubes were sterilized with ethylene oxide gas. The water content of PS-1 and that of PS-2 were 35% and 8.2%, respectively.

Three mongrel dogs (about 15 kg. each) were anesthetized by intravenous injection of sodium pentobarbital and their dexter coxal vein was incised. Then, these tubes and a tube formed from a soft polyvinyl chloride having the same diameter were inserted from the incised portion up to near the inlet of the atrium dextrum of the inferior vena cava. After indwelling for 5 days, blood was removed, the abdomen was incised, the inferior vena cava was opened and the state of the formation of thrombus on the material surface was observed. Furthermore, the portion free from thrombus was sampled and checked for the amount of adsorbed protein by amino acid analysis.

The results are as shown in Table 3. Formation of thrombus was recognized on the surface of the soft polyvinyl chloride tube and of PS-2 tube. Also in the portion free from thrombus there was observed the adsorption of a large amount of plasma protein.

On the other hand, on the surface of PS-1 tube formed from the hydrogel of the present invention there was formed little thrombus, and the amount of protein adsorbed thereto was as small as less than one-tenth of the former two. Thus, PS-1 tube exhibited superior antithrobogenicity and biocompatibility.

TABLE 3

Evaluation results of antithrombogenicity according to the inferior vena cava indwelling catheters method

| Dog No. | Sample | Formation of thrombus*1 | Amount of protein adsorbed*2 |
|---|---|---|---|
| 1 | Soft polyvinyl chloride | Yes | 8 μg/cm² |
| 2 | PS-1 | No | 0.2 μg/cm² |
| 3 | PS-2 | Yes | 6.4 μg/cm² |

*1Judged by observing the material surface visually
*2Measured with respect to the portion free from thrombus

EXAMPLE 4

50 g. of polyvinyl chloride with a degree of polymerization of 1,100 containing 0.032 mol% of diethyldithiocarbamate groups as photosensitive groups and 50 g. of methoxypolyethylene glycol methacrylate (M-9G) having polyethylene glycol units with a degree of polymerization of 9 were dissolved in 500 g. of tetrahydrofuran and then irradiated at 30° C. for 8 hours under an argon gas stream using a high-pressure mercury lamp ("UM-102" manufactured by Ushio Denki Co.) in a light source immersion type photo reactor ("ULO-6DQ" manufactured by Ushio Denki Co.) to obtain a graft copolymer.

Elementary analysis of this graft copolymer was as tabulated below.

| | C | H | N | Cl |
|---|---|---|---|---|
| Polyvinyl chloride, trunk polymer | 38.5% | 4.9% | 0% | 55.8% |
| Graft polymer | 49.5% | 7.3% | 0% | 16.8% |

From the above elementary analysis values, this graft copolymer proved to contain 69.8% by weight of M-9G. The graft copolymer was dissolved in dimethylformamide and then formed into a film according to the solvent casting method. The water content of the film were 63.7%.

EXAMPLE 5

250 g. of a vinyl chloride—vinyl acetate—ethylene copolymer ("Graftmer $R_3$" manufactured by Nippon Geon Co., vinyl chloride unit content 56 mol%) containing 0.05 mol% of diethyldithiocarbamate groups and 150 g. of methoxypolyethylene glycol methacrylate (M-23G) having polyethylene oxide units with a degree of polymerization of 23 were dissolved in 5 liters of cyclohexanone and then irradiated at 30° C. for 6 hours under a nitrogen gas stream using a 450 W high-pressure mercury lamp ("UM-452" manufactured by Ushio Denki Co.) disposed at a distance of 10 cm from the reaction vessel to obtain a graft copolymer with M-23G grafted to "Graftmer $R_3$".

Elementary analysis of this graft copolymer was as tabulated below.

| | C | H | N | Cl |
|---|---|---|---|---|
| Graftmer $R_3$, trunk polymer | 50.5% | 6.5% | 0% | 36.0% |
| Graft copolymer | 52.3% | 8.0% | 0% | 25.5% |

From the above elementary analysis values, this graft copolymer proved to contain 29.2% by weight of M-23G.

EXAMPLE 6

The graft copolymer prepared in Example 4 was dissolved in N,N-dimethylformamide to a concentration of 5% and formed into a tube by the dipping method using as a core a stainless steel rod 1.5 mm in diameter and about 30 cm long. After extraction in 60° C. methanol and water for 3 days each, the tube was vacuum-dried and then sterilized with ethylene oxide gas.

An mongrel dog (about 15 kg.) was anesthetized by intravenous injection of sodium pentobarbital and its dexter coxal vien was incised. Then, the tube was inserted from the incised portion up to near the inlet of the atrium dextrum of the inferior vena cava. After indwelling for 5 days, blood was removed, the abdomen was incised, the inferior vena cava was opened and the state of formation of thrombus on the material surface was observed. As a result, there was recognized little thrombus on the surface of the tube formed from the graft copolymer of the present invention, and this material proved to exhibit a superior antithrombogenicity and have properties useful as a biomedical material.

What is claimed is:

1. An antithrombogenic biomedical material comprising a graft copolymer obtained by graft copolymerization not less than 5% by weight, based on total weight of the monomers constituting the graft copolymer, of one or more polymerizable monomers (A) having a polyethylene oxide unit with a degree of polymerization not less than 5 and a polymerizable carbon-carbon double bond onto a polymer (B) obtained by polymerization of one or more monomers copolymerizable with the monomer or monomers A, wherein said polymer (B) is a polymer or copolymer containing not less than 10% by weight, in terms of monomer, of vinyl chloride units.

2. The biomedical material of claim 1 wherein the amount of said monomer (A) is in the range of 10 to 95% by weight.

3. The biomedical material of claim 1 wherein the amount of said monomer (A) is in the range of 15 to 90% by weight.

4. The biomedical material of any one of claim 1 through 3 wherein the equilibrium water content at 25° C. of said copolymer is in the range of 5 to 90%.

5. The biomedical material of claim 4 wherein the equilibrium water content of said copolymer is in the range of 20 to 70%.

6. The biomedical material of claim 1 wherein said monomer (A) is a compound represented by the formula

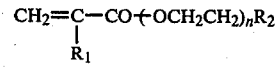

or the formula

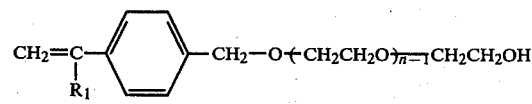

where $n \geq 5$, $R_1$ is hydrogen or $CH_3$ and $R_2$ is hydroxyl, $C_1$-$C_4$ alkoxy or $OCHPh_2$ where Ph is phenyl.

7. The biomedical material of claim 6 wherein n in the formulae is an integer ranging from 9 to 300.

8. The biomedical material of claim 1 wherein said polymer (B) is polyvinyl chloride.

9. The biomedical material of claim 1 wherein said polymer (B) is vinyl-chloride-vinyl acetate copolymer or vinyl chloride-vinyl acetate-ethylene terpolymer.

* * * * *